United States Patent
Colin

(10) Patent No.: US 7,259,021 B2
(45) Date of Patent: Aug. 21, 2007

(54) METHOD FOR USING A TEST CARD

(75) Inventor: Bruno Colin, Marcy (FR)

(73) Assignee: Bio Merieux, Marcy l'Etoile (FR)

( * ) Notice: Subject to any disclaimer, the term of this patent is extended or adjusted under 35 U.S.C. 154(b) by 593 days.

(21) Appl. No.: 10/220,845

(22) PCT Filed: Mar. 6, 2001

(86) PCT No.: PCT/FR01/00668

§ 371 (c)(1),
(2), (4) Date: Oct. 1, 2002

(87) PCT Pub. No.: WO01/66250

PCT Pub. Date: Sep. 13, 2001

(65) Prior Publication Data

US 2003/0148535 A1 Aug. 7, 2003

(30) Foreign Application Priority Data

Mar. 7, 2000 (FR) .................................. 00 02931

(51) Int. Cl.
*G01N 1/10* (2006.01)
(52) U.S. Cl. ..................................... 436/180; 422/100
(58) Field of Classification Search ............... 422/100; 436/180
See application file for complete search history.

(56) References Cited

U.S. PATENT DOCUMENTS

| | | | |
|---|---|---|---|
| 3,859,090 A * | 1/1975 | Yoerger et al. | 430/276.1 |
| 4,253,846 A | 3/1981 | Smythe et al. | |
| 4,789,717 A * | 12/1988 | Giannetti et al. | 526/209 |
| 5,302,515 A | 4/1994 | Goodwin, Jr. | |
| 5,554,339 A | 9/1996 | Cozzette et al. | |
| 5,763,278 A | 6/1998 | Sickinger et al. | |
| 5,841,039 A | 11/1998 | Uffenheimer | |
| 5,843,380 A | 12/1998 | Staples et al. | |
| 5,853,894 A * | 12/1998 | Brown | 428/422 |
| 5,856,174 A | 1/1999 | Lipshutz et al. | |
| 6,015,531 A | 1/2000 | Colin et al. | |

FOREIGN PATENT DOCUMENTS

| | | |
|---|---|---|
| EP | 0 381 501 | 8/1990 |
| FR | 2 749 663 | 12/1997 |
| FR | 2 782 934 | 3/2000 |
| FR | 2 782 935 | 3/2000 |
| FR | 2 795 476 | 12/2000 |
| WO | WO95/33846 | 12/1995 |
| WO | WO97/02357 | 1/1997 |
| WO | WO97/27324 | 7/1997 |

* cited by examiner

*Primary Examiner*—Jill Warden
*Assistant Examiner*—Paul S Hyun
(74) *Attorney, Agent, or Firm*—Oliff & Berridge, PLC

(57) ABSTRACT

The present invention relates to a method for using a test card (1) comprising at least one fluid circuit, constituting a network of channels (3) and/or of compartments (17), for transferring at least one biological liquid from at least one inlet (2) to at least one outlet (6, 17), and a hydrophobic fluid is injected into the test card, into all or part of the network of said card, prior to the transfer of the biological liquid(s), said hydrophobic fluid filling the capillary spaces formed by the angles of the network of channels and/or of compartments of the card and avoiding the formation of bubbles and/or of dead volumes during the transfer of the biological liquid.

The invention is of preferential use in the field of microfluidics applied to biology.

8 Claims, 2 Drawing Sheets

Section A-A

METHOD FOR USING A TEST CARD

The present invention relates to a method for using a test card comprising at least one fluid circuit, constituting a network of channels and/or compartments, for transferring a liquid within the card, using a hydrophobic fluid. The invention also relates to the test card.

The state of the art consists of document U.S. Pat. No. 5,554,339 which describes a sampler for delivering small volumes of liquid via a needle. The outer surface of the needle is covered with a hydrophobic fluid which decreases the adhesion, to the needle, of the drop of liquid to be delivered and thus makes it possible to increase the precision regarding small volumes. The same principle is described in U.S. Pat. No. 5,763,278 for an automatic device for pipetting small volumes with a needle.

Documents U.S. Pat. Nos. 4,253,846 and 5,841,039 describe an apparatus for the automated analysis of liquid samples, in which a segment of sample liquid, separated by a segment of air, circulates in the conduits of the apparatus via a hydrophobic carrier fluid immiscible with the sample, which is generally aqueous. The role of this carrier fluid is to encapsulate each sample segment so as to isolate them from one another and thus decrease intersample contamination.

Test cards with fluid circuits which can be used on automated devices have been described, for example, in the Applicant's patents or patent applications U.S. Pat. No. 5,843,380 or FR 2 749 663. Test cards are most commonly disposable consumables. It is particularly important to control the costs of manufacturing such cards for economic reasons. For the same economic reasons, and because biological tests use increasingly small volumes of the order of a nanoliter to a few tens of microliters, miniaturization of the cards, and therefore of the fluid circuits within these cards, is a high stakes project. One of the essential problems of transferring liquid in this type of card is linked to the formation of bubbles or foam which prohibit precise positioning of the liquid in a given zone and are detrimental to the analysis.

This phenomenon is further accentuated by the presence in the biological liquids, which are moved within the cards, of surfactants or detergents such as SDS (Sodium Dodecyl Sulfate), Tween® or Triton®.

In theory, it is possible to produce cards in which there is no discontinuity of shape in the fluid circuit, in particular using rounded edges, which minimizes this phenomenon, but the cost of manufacturing theses cards is prohibitive. In practice, test cards obtained by molding have, in a first step of the manufacturing process, a fluid circuit similar to a cavity and open to the outside with at least one sharp edge at the surface which corresponds to the imprint of the part which created the cavity. To ensure that the card is leaktight, these cards are either sealed with an adhesive film (see, for example, the Applicant's patent applications or patents U.S. Pat. No. 5,843,380 or FR 2 749 663) or the card is manufactured as two components and these two components are assembled, for example by adhesive bonding or heat welding (see, for example, WO 95/33846). Capillary spaces and sharp edges which promote the formation of bubbles (or foam) are created and there is liquid retention due to the creation of dead volumes.

The present invention solves the problems mentioned above by providing a simple technique applicable to test cards.

In particular, the present invention relates to a method for using a test card comprising at least one fluid circuit, constituting a network of channels and/or of compartments, for transferring al least one biological liquid from at least one inlet to at least one outlet, in which a hydrophobic fluid is injected into all or part of the network of said card, prior to the transfer of the biological liquid(s), said hydrophobic fluid filling the capillary spaces formed by the angles of the network of channels and/or of compartments of the card and avoiding the formation of bubbles and/or of dead volumes during the transfer of the biological liquid.

The use of such a card concerns the analysis of one or more different liquid samples in which the identification of one or more analytes is sought using all the simple or complex analytical processes which use one or more different reagents depending on the chemical, physical or biological nature of the analyte(s) being sought. The technical principles defined below are not limited to a particular analyte, the only condition required being that the analyte is distributed in the sample to be analyzed in suspension or solution. In particular, the analytical process used may be performed in homogeneous or heterogeneous or mixed form.

A particular nonlimiting mode of such a card relates to the biological analysis of one or more ligands which require the use of one or more antiligands in order to be detected and/or quantifed. The term "ligand" is intended to mean any biological species, such as, for example, an antigen, an antigen fragment, a peptide, an antibody, an antibody fragment, a hapten, a nucleic acid, a nucleic acid fragment, a hormone or a vitamin. An example of application of the analytical techniques relates to direct analysis or competition immunoassays, whatever their format. Another example of application relates to the detection and/or quantification of nucleic acids, comprising all the operations required for this detection and/or this quantification using any sample containing the target nucleic acids. Among these various operations, mention may be made of lysis, fluidification, concentration, enzymatic nucleic acid amplification steps and detection steps incorporating a hybridization step using, for example, a DNA chip or a labeled probe.

The term "hydrophobic fluid" is intended to mean a hydrophobic liquid, such as, for example, fluoro or perfluoro hydrocarbons or silylated oils, for instance dimethylsiloxane oils with a trimethylsilyl ending. The hydrophobic fluid is preferably an oil with a low kinematic viscosity. The term "kinematic viscosity" is preferably intended to mean between 1 centistoke and 100 centistokes, advantageously between 4 centistokes and 50 centistokes, at 40° C. This viscosity scale enables the oil to perform its function of filling the capillary spaces but without blocking the fluid circuit, and therefore allow the analysis to be carried out.

Surface tension is another parameter of the hydrophobic fluid to be taken into consideration by those skilled in the art, depending on the type of material used for the test card.

The kinematic viscosity is measured using a Cannon-Fenske tube calibrated according to the ASTM D-445, IP71 and ISO-3104 standards at 40° C.

The term "capillary space" is intended to mean the discontinuities in shape within the card and which may lead to liquid retention and to the formation of bubbles, and in particular the angular shapes with an angle of between 0 and 180°, and in particular between 0 and 90°.

The term "biological liquid" is intended to mean all the liquids required for carrying out the analysis. This includes: the biological sample which contains the analyte(s) to be assayed and which is pretreated such as with a lysis step, a fluidification step, a centrifugation step and/or a preculturing step, for example on solid medium which may be diluted in a suitable buffer or used untreated as in the case of serum; the washing, elution and reaction buffers.

The term "test card" is intended to mean a device, preferably a disposable device, comprising at least one inlet, an outlet either outside or within the card, a fluid circuit between the inlet and the outlet and means for controlling the fluid circuit, such as, for example, valves. Many descriptions of valves which can be used in a test card exist in the prior art, such as, for example, in U.S. Pat. No. 5,856,174 or the valves described in the published patent applications FR 2 782 934 and FR 2 782 935 entitled "dispositif permettant des réactions, système de transfert entre dispositifs et procéd éde mise en oeuvre d'un tel système" (device for reactions, system of transfer between the devices and method for implementing such a system) or FR 2 795 476 entitled "vanne permettant de diriger un fluide dans une carte d'analyse" (valve for directing a fluid in a test card), and in particular illustrated in FIGS. 4 to 6. Means for transferring liquid, such as pumps, or means for regulating temperature may be integrated into the test card (see, for example, WO 97/02357).

The term "fluid circuit" is intended to mean a network of channels and/or compartments which make it possible to convey a liquid from an inlet point on the card to a point of outlet towards the outside or the inside of the card. In a particular embodiment of the invention, and in particular in the case of analysis in which the problem of contamination is considerable, such as for analyses involving an enzymatic amplification reaction, the liquids which enter the card do not leave it, which makes it possible to prevent release of the nucleic acids into the atmosphere (see, for example, patent application EP 0,381,501 or WO 97/27324 which propose an apparatus for carrying out nucleic acid amplifications using the polymerase chain reaction (PCR) technology). In this case, the outlet point on the test card is inside the card, such as, for example, a compartment which acts as a bin.

In terms of production, the test card is obtained by machining a technical plastic, preferably a hydrophobic plastic, such as, for example, the high-impact polystyrene, reference R540E, of the company GOODFELLOW or polypropylene. In an industrial embodiment, the card is obtained by molding.

The nature of the flexible film may vary depending on the nature of the test card and of the fluids tested, in particular for reasons of compatibility. For example, a TPX (polymethylpentene) or BOPP (biaxially oriented polypropylene) polymer film allows biological tests to be carried out. These films may be attached by adhesive bonding (coating of adhesive, such as, for example, silicone adhesives, onto the film) or by welding. An example of adhesive BOPP is provided by the company BioMérieux Inc (St. Louis, Mo., USA) under the reference 022004-2184.

In a first particular embodiment of the invention, a hydrophobic fluid is injected into the card, into the entire network of said card, prior to the transfer of biological liquids.

In a second particular embodiment of the invention, between the step of injecting the hydrophobic fluid and before the transfer of biological liquid in the test card, the excess hydrophobic fluid is removed with a second fluid. In particular, the excess hydrophobic fluid is eliminated by circulating a gas, preferably air.

In another embodiment of the invention, a predetermined amount of hydrophobic fluid is injected into the card, this amount being sufficient to coat all or part of the fluid circuit in order to avoid the formation of bubbles and/or of dead volumes. For example, if the card is used in an automated analytical device, the hydrophobic fluid is injected into the card in a prior step and the biological liquid(s) is (are) introduced into the card after this step.

The invention also relates to a test card comprising at least one fluid circuit constituting a network of channels and/or compartments for transferring at least one biological liquid from at least one inlet to at least one outlet, in which all or part of the network of the card is coated with a hydrophobic fluid filling the capillary spaces formed by the angles present on the network of channels and/or compartments of the card and avoiding the formation of bubbles and/or dead volumes during the transfer of the biological liquid. Said card is preferably substantially flat and said card is covered with a flexible film. In particular, said card is substantially in the shape of right-angled parallelepiped, at least one face of which is flat, at least one flat face being machined or molded so as to form the fluid circuit, and said card is covered with at least one flexible film delimiting said fluid circuit.

The attached figures and example are in no way limiting in nature. They will make it possible to understand the invention more clearly.

Figure 1:
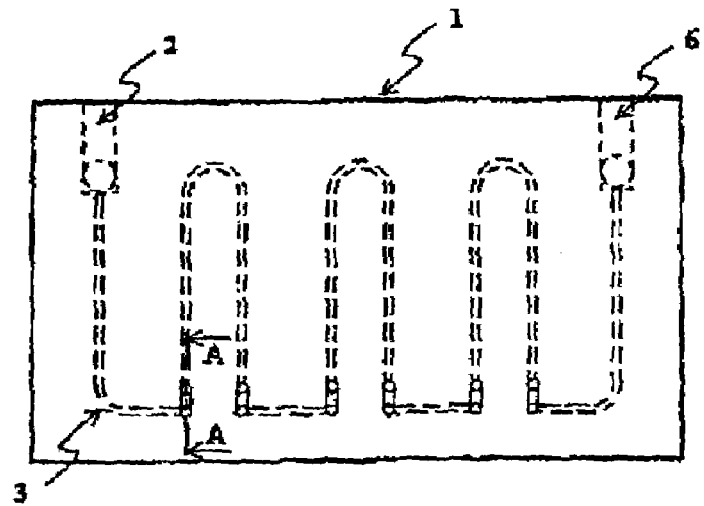
FIG. 1 represents a view of one of the faces of a simplified test card comprising a single reaction path.

FIG. 1 represents a simplified test card 1 comprising an inlet 2 with a fluid circuit consisting of a channel 3 to an outlet 6.

Figures 2, 3:
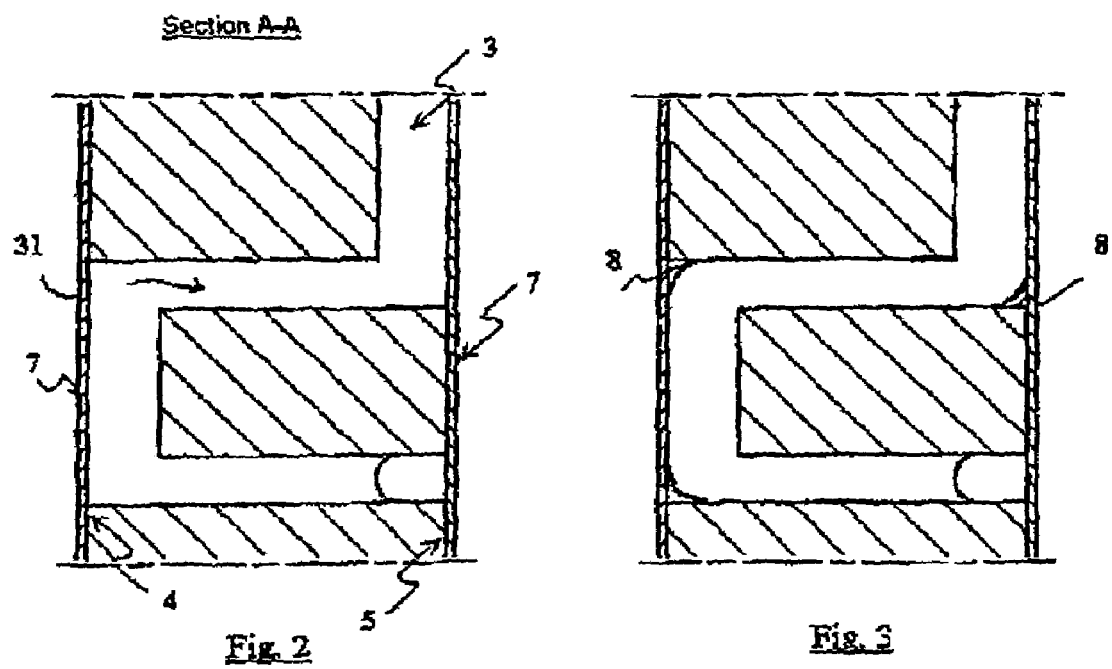
FIG. 2 represents a sectional view along A-A of this test card before the method is carried out.
FIG. 3 represents an identical sectional view of this test card after the method is carried out.

On the section A-A of FIG. 2, the substantially flat shape of the test card is seen, with the lower faces 4 covered with a flexible film 7 and an upper face 5 covered with a flexible film 7. This card has a cross channel 31 which generates right angles and therefore capillary spaces on the card. The hydrophobic liquid fills these capillary spaces as represented on FIG. 3, forming a rounded edge 8 which makes it possible to avoid the formation of bubbles. The method according to the invention is particularly suitable when the test card is substantially flat with at least one cross channel 31. In fact, it is very difficult and therefore expensive to recreate the rounded edge during the process of manufacturing the card, in particular in a molding process in which the part used to create the channel must be able to re-exit, the effect of which is to create a sharp edge. At the macroscopic level, as represented on these figures, a right angle is visible with rectilinear edges, but at the microscopic level, of course, the surface finishes show rough patches which increase the phenomenon of bubble formation and further justify the advantage of the method according to the invention.

Figure 4:
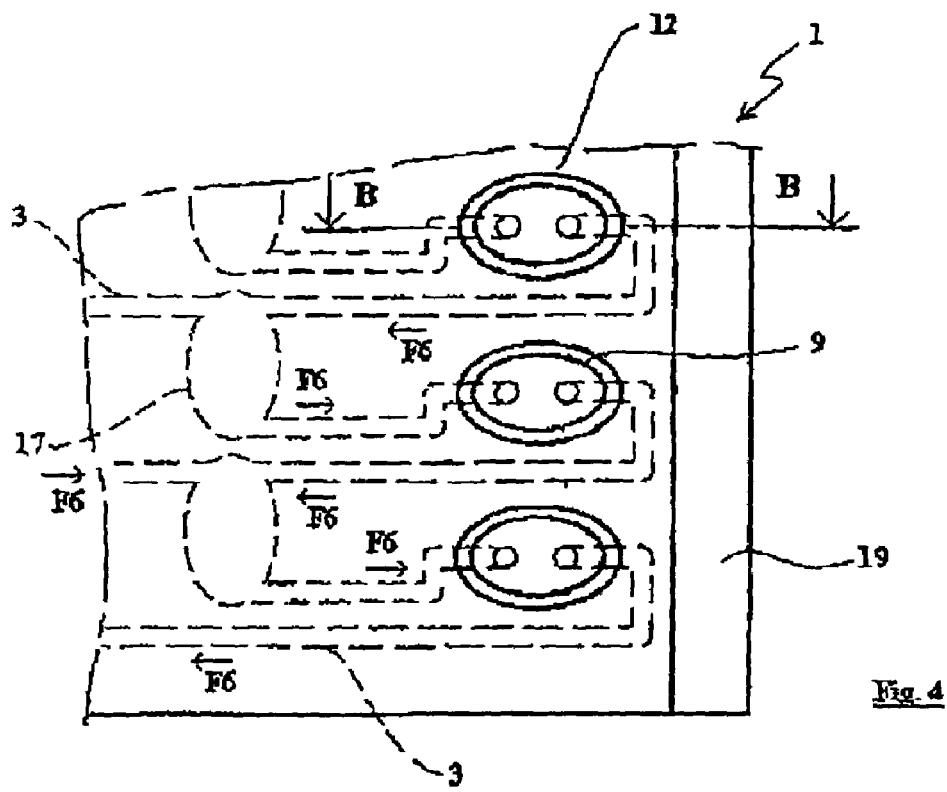
FIG. 4 represents a partial view of a test card comprising valves.

FIG. 4 represents a view from above of a test card comprising a fluid circuit comprising channels, compartments and valves. In this case, it is noted that each valve 12 consists of a small flat surface located at the same level as the rest of the flat surface of said card 1 (see also FIGS. 5 and 6), this small surface comprising at least one entry channel 3 and one exit channel 3, the point of intersection between this surface and the channels 3 for entry and exit of the fluid being in contact with the film 7, as is clearly represented on FIG. 5. In this case, the valve is closed; moreover, on FIG. 5 a stud made of an elastomer 11, the function of which is to close the valve, is noted. This stud is represented schematically, in order to clearly show that it blocks one of the two channels 3. Of course, the stud 11 may block one or the other of the channels or both channels 3. In addition, there may be more channels, i.e. three or more, at the level of the valve.

It is also noted that the card comprises a certain number of compartments 17. The compartments 17 are connected to the valves via the channels 3 and it is possible, but this is not represented on the figure, for other valves and other compartments to be present on the rest of the card 1, which makes it possible to perform mixing between two networks of channels 3 located in parallel and no longer in series. This is clearly represented in FIG. 4, in which it is noted that the fluid movements along F6 on the card may bring together two liquids so as to perform mixing or an analysis in a compartment 17. In the case of a closed card, a compartment 17 may act as a bin and therefore as an outlet for the hydrophobic liquid.

Figure 5:
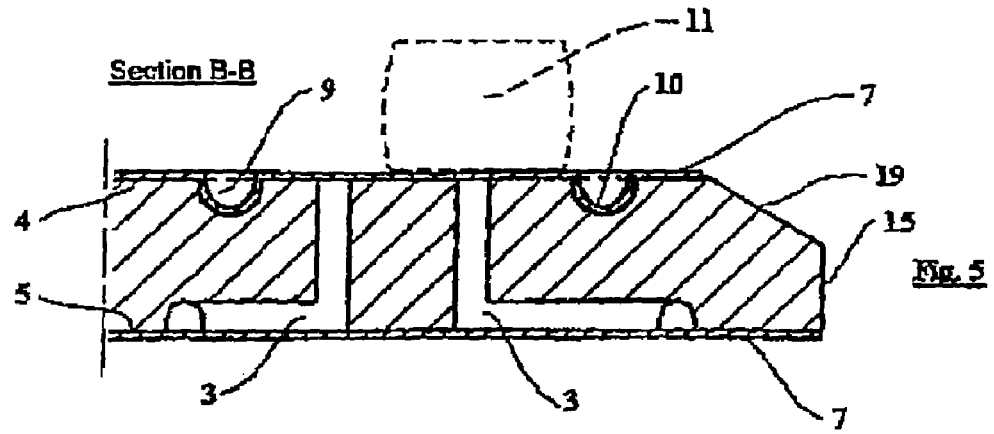
FIG. 5 represents a sectional view along B-B of FIG. 4, when the valve is in the closed position.
Figure 6:
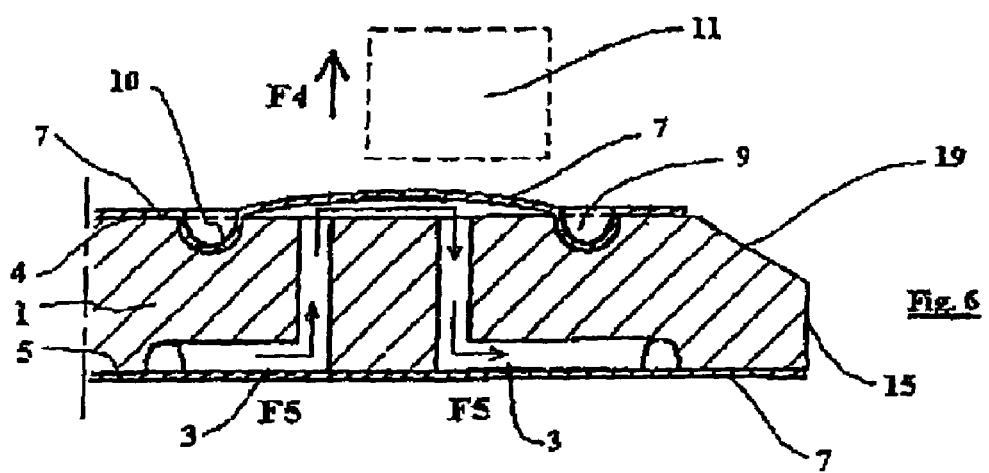
FIG. 6 represents a sectional view identical to FIG. 5, when the valve is in the open position.

On FIGS. 5 and 6 it is now noted that there is a flexible film 7 over the upper valve 4 of the card 1. This film 7, which in this particular case is not self-adhesive, is therefore welded at 10 in the region of a groove 9 peripheral to the valve 2. Of course, it is also possible to have a second flexible film 7 over this other face. The upper 4 and lower 5 faces are connected to one another via an edge 15 on which there is a beveled surface 19 on at least one of the sides, as represented on FIGS. 4 to 6.

In fact, the fluid(s) present in the test card 1 are moved within this card 1 by increasing pressure or by creating a partial vacuum. The movement of the fluid in a direction of F5 of FIG. 6 is produced by raising the stud 11 in a direction F4, such that it will be possible to distort the flexible film, and the fluid may pass in a direction of F5 as is clearly represented.

EXAMPLE 1

In order to verify the effectiveness of the method according to the invention, a test card (25 mm by 25 mm in size, thickness 3.5 mm) with a conical inlet and outlet 2 mm in diameter is manufactured, according to FIG. 1, by machining a hydrophobic technical plastic made of high-impact polystyrene, reference R540E, from the company GOODFELLOW. The channel is obtained via a milling cutter head 0.5 mm in diameter along the card. The card is covered with a BOPP adhesive film provided by the company BioMérieux Inc. (St. Louis, Mo. USA) under the reference 02004-2184. 5 microliters of a biological buffer containing 10 mM Hepe; pH 7.5; 150 mM NaCl; 0.1% SDS and 1% of Foam Ban (antifoaming agent sold by the company Ultra Additives Inc. under the reference MS-575) are injected by applying a partial vacuum to the outlet of the card. Without prior treatment of the card, the 5 microliters of biological buffer are transformed into a continuous chain of foam. If prior to this same biological liquid, an oil of the silicone type with a kinematic viscosity of 50 centistokes (Dow Corning reference silicone oil 200 viscosity 50 cs, batch No., X 2034633) is injected, the excess of which in the card is removed by drawing it out, the liquid circulates in the card without foam, which makes it possible to control its position in the card at any time. The same result is obtained with an oil having a kinematic viscosity of 10 centistokes (Dow Corning, reference silicone oil 200 viscosity 10 cs, batch No. XZ034181) and a biological buffer containing 75 mM Tris pH 7.7; 2.5% Triton X100; [lacuna] % glycerol and 1% of Foam Ban. Although in all cases the biological liquid contains an antifoaming agent at a high concentration, i.e. more than 0.5%, the problem of foaming remains considerable in this type of consumable and implementation of the method according to the invention remains necessary.

On the other hand, with an oil of the same nature having a kinematic viscosity of 128 centistokes, the amount of oil trapped in the circuit is too great and the biological liquid cannot circulate. The function of the hydrophobic liquid is therefore clearly to fill the capillary spaces, and only the capillary spaces, so as to prevent the formation of foam and the formation of dead volumes, but without hindering the subsequent circulation of the biological liquids.

The prefilled card is stable for at least two weeks at ambient temperature.

The same effectiveness of the hydrophobic oil in avoiding the problem of bubbles is obtained with a test card as represented in FIG. 4 and which has, by virtue of the arrangement of its fluid circuit, many capillary spaces and 90° sharp edges possibly generating bubbles in the biological liquids.

EXAMPLE 2

In order to verify the compatibility of the oil with enzymatic amplification reactions, a PCR amplification reaction is carried out on a range of purified type 3 poliovirus genomic RNA (from 10 to $10^6$ copies), according to the conditions of the SuperScript™ One-Step™ RT-PCR System Kit (Life Technologies), and using the amplification primers described by P. M. Regan and A. B. Margolin (J. Virological Methods, 64, p 65-72, 1997). To verily the impact of the oil, 20 microliters of oil (Dow Corning 50 cs) are added to 50 microliters of the PCR reaction. Tubes without oil are prepared as a control. After reaction, the amplification products are analyzed by gel electrophoresis on 2% agarose gel and stained with ethidium bromide. The results show the presence of the expected 195-base pairs band with an identical sensitivity limit of 10 copies of target for the tube with oil and for the tube without oil. The oil therefore has no inhibitory effect on the amplification reaction. It is therefore possible to carry out this type of biological reaction in a card in which the capillary spaces are filled with a hydrophobic fluid such as a silylated oil (of the silicone type) without affecting the sensitivity of the biological test.

The invention claimed is:

1. A method of using a test card comprising at least one fluid circuit having capillary spaces, the method comprising the steps of:
    injecting a hydrophobic fluid into the at least one fluid circuit constituting a network of at least one of channels or compartments, such that the entire network of channels is filled with the hydrophobic fluid;
    removing any excess hydrophobic fluid with a second fluid such that only capillary spaces formed by angles of the network are filled with hydrophobic fluid, the hydrophobic fluid forming rounded edges, thereby avoiding formation of bubbles in the capillary spaces and/or of dead volumes during transfer of a biological liquid; and
    transferring at least one biological fluid from at least one inlet to at least one outlet of the fluid circuit.

2. The method as claimed in claim 1, characterized in that the second fluid is a gas.

3. The method as claimed in claim 1, characterized in that a predetermined amount of hydrophobic fluid is injected into the card, this amount being sufficient to coat all or part of the fluid circuit in order to avoid the formation of bubbles and/or dead volumes.

4. The method as claimed in claim 1, characterized in that the hydrophobic fluid has a kinematic viscosity of between 1 and 100 centistokes at 40° C.

5. The method as claimed in claim 1, characterized in that the hydrophobic fluid is a silylated oil.

6. The method as claimed in claim 2, wherein said gas is air.

7. The method as claimed in claim 4, wherein the hydrophobic fluid has a kinematic viscosity between 4 and 50 centistokes at 40° C.

8. The method as claimed in claim 1, wherein the excess fluid is a volume of the hydrophobic fluid injected into the test card minus the volume of the hydrophobic fluid filling the capillary spaces.

* * * * *